(12) United States Patent
Lansalot-MaTras et al.

(10) Patent No.: US 8,530,592 B2
(45) Date of Patent: Sep. 10, 2013

(54) CATALYST COMPONENTS BASED ON FULVENE COMPLEXES

(75) Inventors: Clément Lansalot-MaTras, Vezin-le-Coquet (FR); Olivier Lavastre, Gahard (FR); Sabine Sirol, Horrues (FR)

(73) Assignee: Total Research & Technology Feluy, Seneffe (FELUY) (BE)

( * ) Notice: Subject to any disclaimer, the term of this patent is extended or adjusted under 35 U.S.C. 154(b) by 600 days.

(21) Appl. No.: 12/670,185

(22) PCT Filed: Jul. 16, 2008

(86) PCT No.: PCT/EP2008/059280
§ 371 (c)(1),
(2), (4) Date: Sep. 24, 2010

(87) PCT Pub. No.: WO2009/013194
PCT Pub. Date: Jan. 29, 2009

(65) Prior Publication Data
US 2011/0034653 A1    Feb. 10, 2011

(30) Foreign Application Priority Data

Jul. 24, 2007 (EP) .................................. 07290934

(51) Int. Cl.
C08F 4/80 (2006.01)
C08F 4/70 (2006.01)
C07F 15/00 (2006.01)

(52) U.S. Cl.
USPC ........ 526/169; 526/169.1; 526/164; 526/161; 526/170; 526/172; 556/138; 556/136; 556/45

(58) Field of Classification Search
USPC ............................ 526/172, 161, 169, 169.1
See application file for complete search history.

(56) References Cited

U.S. PATENT DOCUMENTS 6,309,997 B1 * 10/2001 Fujita et al. .................. 502/167

FOREIGN PATENT DOCUMENTS

EP    1 997 834 A1 * 12/2008

* cited by examiner

*Primary Examiner* — Rip A. Lee

(57) ABSTRACT

The present invention discloses metallic complexes based on hydroxyl-carbonyl fulvene ligands, their method of preparation and their use in the oligomerization or polymerization of ethylene and alpha-olefins.

14 Claims, 2 Drawing Sheets

CATALYST COMPONENTS BASED ON FULVENE COMPLEXES

CROSS-REFERENCE TO RELATED APPLICATIONS

This application claims the benefit of PCT/EP2008/059280, filed Jul. 16, 2008, which claims priority from EP 07290934.4, filed Jul. 24, 2007.

The present invention discloses catalyst components based on hydroxyl-carbonyl fulvene ligands their method of preparation and their use in the polymerisation of olefins.

Several ligands have been described in literature, some of which were tested in complexation with metals but none of them have been used as catalysts for the polymerisation of ethylene or alpha-olefins. Some ligands are described for example in Lloyd and Preston (D. Lloyd, N. W. Preston, J. Chem. Soc. C, 1969, 2464-2469.) or by Linn and Sharkey (W. J. Linn, W. G. Sharkey J. Am. Chem. Soc. 1957, 79, 4970-2.) or in Snyder et al. (C. A. Snyder, J. P. Selegue, N. C. Tice, C. E. Wallace. M. T. Blankenbuehler, S. Parkin, K. D. E. Allen, R. T. Beck, J. Am. Chem. Soc. 2005, 127, 15010-11.) or in Dong et al. (Y. B. Dong, Y. Geng, J. P. Ma and R. Q. Huang, Inorg. Chem. 2005, 44, 1693-1703.)

There is a need to develop new catalyst system having good activity and able to produce polymers tailored to specific needs.

It is an aim of the present invention to prepare new catalyst components that can be used in the polymerisation of olefins.

It is also an aim of the present invention to provide very active catalyst components.

It is another aim of the present invention to provide a method for polymerising or copolymerising olefins.

The present invention reaches, at least partially, any one of those aims.

Accordingly, the present invention discloses a method for preparing a metallic complex that comprises the steps of:
a) providing a metallic precursor $MZ_n$ wherein M is a metal Group 6 to 11 of the Periodic Table, Z is a negative counter-anion and n is the valence of M;
b) complexing the metallic precursor of step a) with an hydroxycarbonyl fulvene ligand of formula

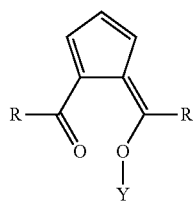

wherein R are the same or different and are selected from aryl, alkyl arylalkyl, alkylaryl having at most 20 carbon atoms or groups containing heteroatoms and Y is an element Group 1 from the Periodic Table.
c) retrieving a metallic complex.

The reaction is carried out in a polar solvent such as tetrahydrofuran (THF) preferably at room temperature.

Preferably, R is selected from alkyl, unsubstituted or substituted phenyl (Ph), CPh2 wherein Ph may be substituted or not, or the R groups include heteroatom-containing units.

More preferably R is a bulky alkyl such as t-butyl or bulkier or contains furan units. Most preferably R is t-butyl or furan.

In a preferred embodiment according to the present invention, the ligand is deprotonated. The deprotonation reaction is carried out before metallation by addition of a base. Most preferably, deprotonation is achieved by addition of one equivalent of NaH to the neutral ligand with liberation of hydrogen.

Preferably Y is H or Na, more preferably it is Na.

Preferably, M is CrII, CrIII or Ni, more preferably, it is CrII or CrIII, most preferably it is CrIII.

Preferably Z is halogen or acetate, more preferably, it is Cl.

Several types of metallic complexes can be formed, one where the metal is coordinated to one ligand and one where the metal is coordinated to two ligands. The relative amounts of each ligand and metal unit depend upon the nature of ligand and of the metal. The amount of ligand must therefore be of at least one equivalent of ligand per metallic equivalent. In another preferred embodiment according to the present invention, the metal is coordinated to two ligands.

The present invention further discloses an active catalyst system comprising the metallic complex and an activating agent having an ionising action.

Suitable activating agents are well known in the art. The activating agent can be an aluminium alkyl represented by formula $AlR^+_n X_{3-n}$ wherein $R^+$ is an alkyl having from 1 to 20 carbon atoms and X is a halogen. The preferred alkylating agents are triisobutyl aluminium (TIBAL) or triethyl aluminium (TEAL).

Alternatively and preferably, it is an aluminoxane and comprise oligomeric linear and/or cyclic alkyl aluminoxanes represented by formula

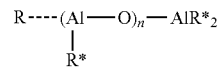

for oligomeric, linear aluminoxanes and by formula

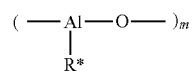

for oligomeric, cyclic aluminoxane,
wherein n is 1-40, preferably 10-20, m is 3-40, preferably 3-20 and R* is a $C_1$-$C_8$ alkyl group and preferably methyl.

The amount of activating is selected to give an Al/M ratio of from 100 to 3000, preferably of about 1000.

Suitable boron-containing activating agents may comprise a triphenylcarbenium boronate such as tetrakis-pentafluo-rophenyl-borato-triphenylcarbenium as described in EP-A-0427696, or those of the general formula $[L'—H]+[B Ar_1 Ar_2 X_3 X_4]-$ as described in EP-A-0277004 (page 6, line 30 to page 7, line 7). The amount of boron—containing activating agent is selected to give B/M ratio of from 0.5 to 5, preferably of about 1.

The preferred activating agent is methylaluminoxane (MAO).

In another embodiment, according to the present invention, the metallic complex may be deposited on a conventional support impregnated with an activating agent. Preferably, the conventional support is silica impregnated with methylaluminoxane (MAO). Alternatively, it can be an activating support such as fluorinated alumina silica.

The present invention further discloses a method for preparing an active catalyst system that comprises the steps of:
a) providing a hydroxyl-carbonyl fulvene ligand;
b) optionally deprotonating the ligand of step a) with a base;
c) complexing the ligand of step a) or of step b) with a metallic salt $MZ_n$ in a solvent;
d) retrieving a catalyst component;
e) optionally depositing the catalyst component of step d) on a support;
f) activating the catalyst component of step d) or of step e) with an activating agent having an ionising action;
g) optionally adding a scavenger;
h) retrieving an active oligomerisation or polymerisation catalyst system.

Alternatively, in step d), the catalyst component is deposited on a support impregnated with an activating agent or on an activating support.

The scavenger may be selected from triethylaluminium, triisobutylaluminum, tris-n-octylaluminium, tetraisobutyl-dialuminoxane or diethyl zinc.

The active catalyst system is used in the oligomerisation and in the polymerisation of ethylene and alpha-olefins.

The present invention discloses a method for the oligomerisation or the homo- or co-polymerisation of ethylene and alpha-olefins that comprises the steps of:
a) injecting the active catalyst system into the reactor;
b) injecting the monomer and optional comonomer;
c) maintaining under polymerisation conditions;
d) retrieving the oligomers and/or polymer.

The pressure in the reactor can vary from 0.5 to 60 bars, preferably from 15 to 45 bars. The productivity of the catalyst system increases with increasing pressure.

The polymerisation temperature can range from 10 to 100° C., preferably from 30 to 55° C. The productivity of the catalyst system decreases with increasing temperature.

Most preferred polymerisation is carried out at a temperature of from 30 to 55° C. and at a pressure of from 24 to 45 bars.

Preferably the monomer and optional comonomer are selected from ethylene, propylene or 1-hexene.

The present invention also discloses the polymers obtained with the new catalyst systems.

LIST OF FIGURES

EXAMPLES

Synthesis of Ligands

Figure 1:
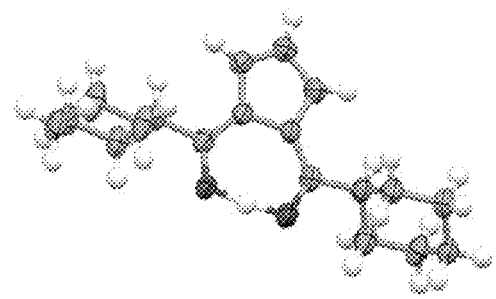
FIG. 1 represents the molecular structure of ligand 1-cyclohexanecarbonyl-6-hydroxy-6-cyclohexanefulvene.

The ligands were prepared following the methods similar to those described for example in Lloyd and Preston (D. Lloyd, N. W. Preston, J. Chem. Soc. C, 1969, 2464-2469.) or by Linn and Sharkey (W. J. Linn, W. G. Sharkey J. Am. Chem. Soc. 1957, 79, 4970-2.) or in Snyder et al. (C. A. Snyder, J. P. Selegue, N. C. Tice. C. E. Wallace. M. T. Blankenbuehler, S. Parkin, K. D. E. Allen, R. T. Beck, J. Am. Chem. Soc. 2005, 127. 15010-11.) or in Dong et al. (Y. B. Dong, Y. Geng, J. P. Ma and R. Q. Huang, Inorg. Chem. 2005, 44, 1693-1703.)

All reactives were purchased from commercially available sources and used without purification and the solvents were purified following standard procedures. The NMR spectra were recorded either on a Brücker ARX 200 spectrometer, at 200 MHz for $^1H$ spectra and at 50 MHz for $^{13}C$ spectra, or on a Brücker AC 300P at 300 MHz for $^1H$ spectra and at 75 MHz for $^{13}C$ spectra. Mass spectra were obtained with a high resolution mass spectrometer Varian MAT 311 and microanalysis were carried out on a Flash EA1112 CHNS/O Thermo Electron (Centre Régional de Mesures des Physiques de l'Ouest, Rennes, France). Crystalline structure were studied with a diffractometer 'Enraf Nonius FR590' NONIUS Kappa CCD.

Preparation of Ligand A:
1-neopentoyl-6-hydroxy-6-tertbutylfulvene

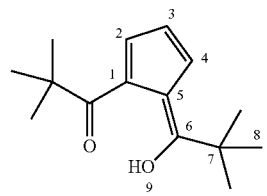

$C_{15}H_{22}O_2$
Mol. Wt.: 234,33
C, 76.88; H, 9.46; O, 13.66
Yellow solid
Yield: 39%

Cyclopentadienyl lithium was prepared from 14.5 mmol of just distilled cyclopentadiene and 14.5 mmol of butyl lithium. A solution of 1.170 g (9.7 mmol) of trimethylacetyle chloride in 20 mL of anhydrous ether was added dropwise to a solution of 14.7 mmol of cyclopentadienyl lithium in 20 mL of anhydrous ether, at a temperature of 0° C. The yellow mixture was placed under stirring overnight at room temperature (about 25° C.). The solvent was evaporated under vacuum and the remaining solid was treated with 20 mL of an acid HCl solution (5% in water) overnight. The product was extracted with 20 mL of ethyl acetate, purified on silica gel ($CH_2Cl_2$/heptane, 1:1) and dried on $MgSO_4$ to afford 440 mg of yellow solid with a yield of 39%.

The ligand was characterised as follows.

$^1H$ NMR ($CDCl_3$, 200 MHz, ppm) δ 19.33 (1H, s, $O^9H$), 7.62 (2H, d, J=0.21 Hz, $C^2H$), 6.39 (1H, s, $C^3H$), 1.48 (18, s, $C^8H_3$).

$^{13}C$ NMR ($CDCl_3$, 50 MHz, ppm) δ: 199.19 ($C^6$), 135.31 ($C^2$ ad $C^4$), 122.36 ($C^1$ and $C^5$), 119.98 ($C^3$), 42.84 ($C^7$), 31.21 ($C^8$).

HRMS: Calcd. for $M^+$ ($C_{15}H_{22}O_2$) m/z=234.16198. found 234.1640.

Anal. Cald for $C_{15}H_{22}O_2$: C, 76.88; H, 9.46; O: 13.66 found C, 76.48; H, 9.40.

Preparation of Ligand B: 1-cyclohexanecarbonyl-6-hydroxy-6-cyclohexanefulvene

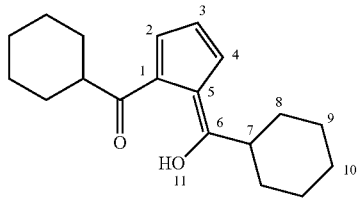

$C_{19}H_{26}O_2$
Mol. Wt.: 286,41
C, 79.68; H, 9.15; O, 11.17
Yellow solid
Yield: 70%

Cyclopentadienyl lithium was prepared from 14.5 mmol of just distilled cyclopentadiene and 14.5 mmol of butyl lithium. A solution of 1.422 g (9.7 mmol) of cyclohexane carbonyl chloride in 20 mL of anhydrous ether was added dropwise to a solution of 14.7 mmol of cyclopentadienyl lithium in 20 mL of anhydrous ether, at a temperature of 0° C. The dark brown mixture was placed under stirring overnight at room temperature (about 25° C.). The solvent was evaporated under vacuum and the remaining solid was treated with 20 mL of an acid HCl solution (5% in water) overnight. The product was extracted with 20 mL of ethyl acetate, purified on silica gel ($CH_2Cl_2$/heptane, 90/10 AIT flash chromatography) and dried on $MgSO_4$ to afford 974 mg of yellow solid with a yield of 70%.

The ligand was characterised as follows.

$^1$H NMR (CDCl$_3$, 200 MHz, ppm) δ 18.78 (1H, s, O$^{11}$H), 7.44 (2H, d, J=0.02 Hz, C$^2$H and C$^4$H), 6.39 (1H, s, C$^3$H), 3.19 (2, t, J=0.05 Hz, C$^7$H), 1.55-1.87 (20H, m, C$^8$H$_2$, C$^9$H$_2$ and C$^{10}$H$_2$).

$^{13}$C NMR (CDCl$_3$, 50 MHz, ppm) δ: 195.26 (C$^6$), 135.84 (C$^2$ and C$^4$), 123.37 (C$^1$ and C$^5$), 121.07 (C$^3$), 45.05 (C$^7$), 31.21 (C$^8$), 26.36 (C$^9$ and C$^{10}$).

HRMS: Calcd. for M$^+$ ($C_{19}H_{26}O_2$) m/z=286.19328. found 286.1939

Calcd. for [M—C$_6$H$_{11}$]$^+$ ($C_{13}H_5O_2$) m/z=203.10720. found 203.1086. Anal. Cald for $C_{19}H_{26}O_2$: C, 79.68; H, 9.15, O: 11.17 found C, 79.54; H, 9.24. Cristallography. Crystals were obtained by slow evaporation of a saturated solution of ligand in tetrahydrofuran (THF). The complex is represented in FIG. 1, and it is characterised are as follows.

| | |
|---|---|
| Emprical formula | $C_{19}H_{26}O_2$ |
| Formula weight | 286.40 |
| Temperature | 120(2) K |
| Wavelength | 0.71073 A |
| Crystal system, space group | Monoclinic, P 21/n |
| Unit cell dimensions | a = 1.34010(3) nm   alpha = 90 deg. |
| | b = 0.92100(3) nm   beta = 117.2020(10) deg. |
| | c = 1.45837(4) nm   gamma = 90 deg. |
| Volume | 1.60089(8) nm$^3$ |
| Z, Calculated density | 4, 1.188 Mg/m$^3$ |
| Absorption coefficient | 0.075 mm$^{-1}$ |
| F(000) | 624 |
| Crystal size | 0.3 x 0.25 x 0.2 mm |
| Theta range for data collection | 2.71 to 27.49 deg. |
| Limiting indices | $-17 <= h <= 17, -11 <= k <= 11, -18 <= l <= 18$ |
| Reflections collected/unique | 6882/3672 [R(int) = 0.0326] |
| Completeness to theta | = 27.49  99.9% |
| Absorption correction | None |
| Refinement method | Full-matrix least-squares on F$^2$ |
| Data/restraints/parameters | 3672/0/193 |
| Goodness-of-fit on F^2 | 1.059 |
| Final R indices [l > 2sigma(l)] | R1 = 0.0517, wR2 = 0.1370 |
| R indices (all data) | R1 = 0.0810, wR2 = 0.1566 |
| Largest diff. peak and hole | 0.230 and -0.226 A$^{-3}$ |

Preparation of Ligand C:
1-benzoyl-6-hydroxy-6-phenylfulvene

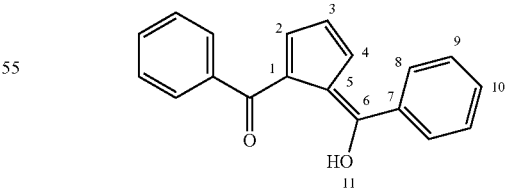

$C_{19}H_{14}O_2$
Mol. Wt.: 274,31
C, 83.19; H, 5.14; O, 11.67
Yellow solid
Yield: 81.5%

Cyclopentadienyl lithium was prepared from 14.5 mmol of just distilled cyclopentadiene and 14.5 mmol of butyl lithium.

A solution of 1.363 g (9.7 mmol) of benzoyl chloride in 20 mL of anhydrous ether was added dropwise to a solution of 14.7 mmol of cyclopentadienyl lithium in 20 mL of anhydrous ether, at a temperature of 0° C. The yellow mixture was placed under stirring overnight at room temperature (about 25° C.). The solvent was evaporated under vacuum and the remaining solid was treated with 20 mL of an acid HCl solution (5% in water) overnight. The product was extracted with 20 mL of ethyl acetate, purified on silica gel ($CH_2Cl_2$/heptane, 70/30 AIT flash chromatography) and dried on $MgSO_4$ to afford 1084 mg of yellow solid with a yield of 81.5%.

The ligand was characterised as follows.

$^1$H NMR ($CDCl_3$, 200 MHz, ppm) δ 18.52 (1H, s, $O^{11}H$), 7.76 (4H, d, J=0.03 Hz, $C^8H$), 7.46-7.75 (6H, m, $C^9H$ and $C^{10}H$), 7.24 (2H, d, J=0.02 Hz, $C^2H$ and $C^4H$), 6.46 (1H, t, J=0.05, $C^3H$).

$^{13}$C NMR ($CDCl_3$, 50 MHz, ppm) δ: 185.80 ($C^6$), 142.12 ($C^{10}$), 138.07 ($C^7$), 131.85 ($C^2$ and $C^4$), 130.18 ($C^9$), 128.61 ($C^8$), 124:80 ($C^1$ and $C^5$), 123.43 ($C^3$).

HRMS: Calcd. for $M^+$ ($C_{19}H_{14}O_2$) m/z=274.09938. found 274.0998

Anal. Cald for $C_{19}H_{14}O_2$: C, 83.19; H, 5.14, O: 11.67 found C, 82.99; H, 5.06.

Preparation of Ligand D: 1-4-tertbutylbenzoyl-6-hydroxy-6-4-tertbutylphenylfulvene

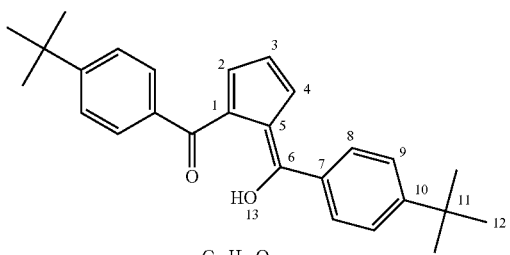

$C_{27}H_{30}O_2$
Mol. Wt.: 386,53
C, 83.90; H, 7.82; O, 8.28
Yellow solid
Yield: 75.5%

Cyclopentadienyl lithium was prepared from 14.5 mmol of just distilled cyclopentadiene and 14.5 mmol of butyl lithium. A solution of 1.908 g (9.7 mmol) of 4-tertbutylbenzoyl chloride in 20 mL of anhydrous ether was added dropwise to a solution of 14.7 mmol of cyclopentadienyl lithium in 20 mL of anhydrous ether, at a temperature of 0° C. The yellow mixture was placed under stirring overnight at room temperature (about 25° C.). The solvent was evaporated under vacuum and the remaining solid was treated with 20 mL of an acid HCl solution (5% in water) overnight. The product was extracted with 20 mL of ethyl acetate, purified on silica gel ($CH_2Cl_2$/heptane, 70/30 AIT flash chromatography) and dried on $MgSO_4$ to afford 1416 mg of yellow solid with a yield of 75.5%.

The ligand was characterised as follows.

$^1$H NMR ($CDCl_3$, 200 MHz, ppm) δ 18.64 (1H, s, $O^{13}H$), 7.77 (4H, d, J=0.04 Hz, $C^8H$), 7.52 (4H, d, J=0.04 Hz, $C^9H$), 7.33 (2H, d, J=0.04, $C^2H$ and $C^4H$), 6.50 (1H, t, J=0.02 Hz, $C^3H$), 1.41 (18H, s, $C^{12}H$).

$^{13}$C NMR ($CDCl_3$, 50 MHz, ppm) δ: 185.76 ($C^6$), 155.45 ($C^{10}$), 141.61 ($C^2$ and $C^4$), 135.61 ($C^7$), 130.23 ($C^9$), 125.61 ($C^8$), 124.72 ($C^1$ and $C^5$), 122.98 ($C^3$), 35.47 ($C^{11}$), 31.68 ($C^{12}$).

HRMS: Calcd. for $M^+$ ($C_{27}H_{30}O_2$) m/z=386.22458. found 386.2210.

Anal. Cald for $C_{27}H_{30}O_2$: C, 83.90; H, 7.82, O: 8.28 found C, 83.64; H, 7.91.

Figure 2:
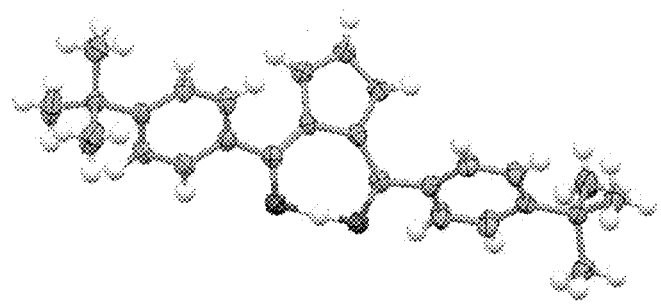
FIG. 2 represents the molecular structure of ligand 1-4-tertbutylbenzoyl-6-hydroxy-6-4-tertbutylphenylfulvene.

Cristallography. Crystals were obtained by slow evaporation of a saturated solution of ligand in THF. The complex is represented in FIG. 2 and it is characterised as follows.

| | |
|---|---|
| Empirical formula | $C_{27}H_{30}O_2$ |
| Formula weight | 386.51 |
| Temperature | 120(2) K |
| Wavelength | 0.071073 nm |
| Crystal system, space group | Monoclinic, P 21/a |
| Unit cell dimensions | a = 1.77026(3) nm    alpha = 90 deg. |
| | b = 0.648020(10) nm   beta = 98.1430(10) deg. |
| | c = 1.89891(3) nm    gamma = 90 deg. |
| Volume | 2.15640(6) nm$^3$ |
| Z, Calculated density | 4, 1.191 Mg/m$^3$ |
| Absorption coefficient | 0.073 mm$^{-1}$ |
| F(000) | 832 |
| Crystal size | 0.35 x 0.3 x 0.3 mm |
| Theta range for data collection | 2.95 to 27.48 deg. |
| Limiting indices | $-22 <= h <= 22, -8 <= k <= 8, -24 <= l <= 24$ |
| Reflections collected/unique | 9424/4932 [R(int) = 0.0326] |
| Completeness to theta | = 27.48   99.6% |
| Absorption correction | None |
| Refinement method | Full-matrix least-squares on $F^2$ |
| Data/restraints/parameters | 4932/0/265 |
| Goodness-of-fit on F^2 | 1.042 |
| Final R indices [I > 2sigma(I)] | R1 = 0.0511, wR2 = 0.1364 |
| R indices (all data) | R1 = 0.0609, wR2 = 0.1463 |
| Largest diff. peak and hole | 0.283 and −0.235 e.A$^{-3}$ |

Preparation of Ligand E: 1-diphenylacetyl-6-hydroxy-6-diphenylfulvene

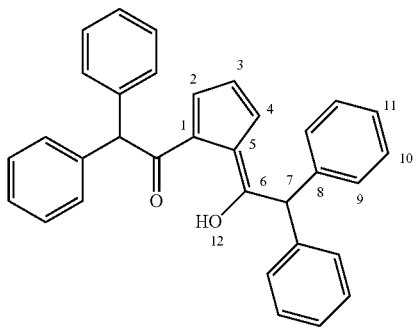

$C_{33}H_{26}O_2$
Mol. Wt.: 454,56
C, 87.20: H, 5.77; O, 7.04
Yellow solid
Yield: 51%

Cyclopentadienyl lithium was prepared from 14.5 mmol of just distilled cyclopentadiene and 14.5 mmol of butyl lithium. A solution of 4.409 g (9.7 mmol) of diphenylacetyl chloride in 20 mL of anhydrous ether was added dropwise to a solution of 14.7 mmol of cyclopentadienyl lithium in 20 mL of anhydrous ether, at a temperature of 0° C. The yellow mixture was placed under stirring overnight at room temperature (about 25° C.). The solvent was evaporated under vacuum and the remaining solid was treated with 20 mL of an acid HCl solution (5% in water) overnight. The product was extracted with 20 mL of ethyl acetate, purified on silica gel ($CH_2Cl_2$/heptane, 1:1) and dried on $MgSO_4$ to afford 1130 mg of yellow solid with a yield of 51%.

The ligand was characterised as follows.

$^1H$ NMR ($CDCl_3$, 200 MHz, ppm) δδ 18.73 (1H, s, $O^{12}H$), 7.63 (2H, d, J=0.02 Hz, $C^2H$ and $C^4H$), 7.27-7.35 (20H, m, $C^9H$, $C^{10}H$ and $C^{11}H$), 6.46 (1H, t, J=0.02, $C^3H$), 5.98 (2H, s, $C^7H$).

$^{13}C$ NMR ($CDCl_3$, 50 MHz, ppm) δ: 189.19 ($C^6$), 140.17 ($C^8$), 138.38 ($C^2$ and $C^4$), 129.53 ($C^{10}$), 129.14 ($C^9$), 127.68 ($C^{11}$), 125.39 ($C^1$ and $C^5$), 122.95 ($C^3$), 57.07 ($C^7$).

HRMS: Calcd. for $M^+$ ($C_{33}H_{26}O_2$) m/z=454.19328. found 454.1978.

Anal. Cald for $C_{33}H_{26}O_2$: C, 87.20; H, 5.77, O: 7.04 found C, 87.26; H, 5.78.

Figure 3:
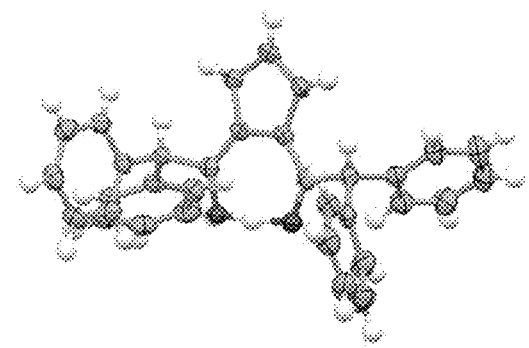
FIG. 3 represents the molecular structure of ligand 1-diphenyl-6-hydroxy-6-diphenylfulvene.

Cristallography. Crystals were obtained by slow evaporation of a saturated solution of ligand in THF. The ligand is represented in FIG. 3 and is characterized as follows.

| | |
|---|---|
| Empirical formula | C33 H26 O2 |
| Formula weight | 454.54 |
| Temperature | 100(2) K |
| Wavelength | 0.071073 nm |
| Crystal system, space group | Monoclinic, C 2/c |
| Unit cell dimensions | a = 3.50497(7) nm   alpha = 90 deg. |
| | b = 0.86045(2) nm   beta = 93.6060(10) deg. |
| | c = 1.61448(4) nm   gamma = 90 deg. |
| Volume | 4.85939(19) $nm^3$ |
| Z, Calculated density | 8, 1.243 $Mg/m^3$ |
| Absorption coefficient | 0.076 $mm^{-1}$ |
| F(000) | 1920 |
| Crystal size | 0.4 x 0.25 x 0.1 mm |
| Theta range for data collection | 2.73 to 27.54 deg. |
| Limiting indices | −45 <= h <= 45, −11 <= k <= 11, −20 <= l <= 20 |
| Reflections collected/unique | 10617/5581 [R(int) = 0.0589] |
| Completeness to theta | = 27.54   99.4% |
| Absorption correction | None |
| Refinement method | Full-matrix least-squares on $F^2$ |
| Data/restraints/parameters | 5581/0/319 |
| Goodness-of-fit on $F^2$ | 1.041 |
| Final R indices [I > 2sigma(I)] | R1 = 0.0605, wR2 = 0.1588 |
| R indices (all data) | R1 = 0.0777, wR2 = 0.1749 |
| Largest diff. peak and hole | 0.312 and −0.374 $e.A^{-3}$ |

Preparation of Ligand F: 1-4-methoxybenzoyl-6-hydroxy-6-4-methoxyphenylfulvene

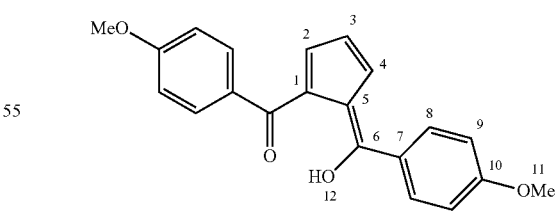

$C_{21}H_{18}O_4$
Mol. Wt.: 334,37
C, 75.43: H, 5.43; O, 19.14
Yellow solid
Yield: 64%

Cyclopentadienyl lithium was prepared from 14.5 mmol of just distilled cyclopentadiene and 14.5 mmol of butyl lithium.

A solution of 1.655 g (9.7 mmol) of 4-methoxybenzoyl chloride in 20 mL of anhydrous ether was added dropwise to a solution of 14.7 mmol of cyclopentadienyl lithium in 20 mL of anhydrous ether, at a temperature of 0° C. The yellow mixture was placed under stirring overnight at room temperature (about 25° C.). The solvent was evaporated under vacuum and the remaining solid was treated with 20 mL of an acid HCl solution (5% in water) overnight. The product was extracted with 20 mL of ethyl acetate, purified on silica gel (Et$_2$O/heptane, 70/30 AIT flash chromatography) and dried on MgSO$_4$ to afford 1040 mg of yellow solid with a yield of 64%.

The ligand was characterised as follows.

$^1$H NMR (CDCl$_3$, 200 MHz, ppm) δ: 18.59 (1H, s, O$^{12}$H), 7.78 (4H, d, J=0.05 Hz, C$^8$H), 7.24 (2H, d, J=0.02 Hz, C$^2$H and C$^4$H), 6.96 (4H, d, J=0.04, C$^9$H), 6.46 (1H, t, J=0.02 Hz, C$^3$H), 3.87 (6H, s, C$^{11}$H).

$^{13}$C NMR (CDCl$_3$, 50 MHz, ppm) δ: 185.06 (C$^6$), 162.93 (C$^{10}$), 140.71 (C$^2$ and C$^4$), 132.48 (C$^8$), 130.52 (C$^5$), 124.48 (C$^7$), 122.59 (C$^3$), 113.96 (C$^9$), 55.92 (C$^{11}$).

HRMS: Calcd. for M$^+$ (C$_{21}$H$_{18}$O$_4$) m/z=334.12051. found 334.1217.

Anal. Cald for C$_{21}$H$_{18}$O$_4$: C, 75.43; H, 5.43, O: 19.14 found C, 75.36; H, 5.38.

Figure 4:
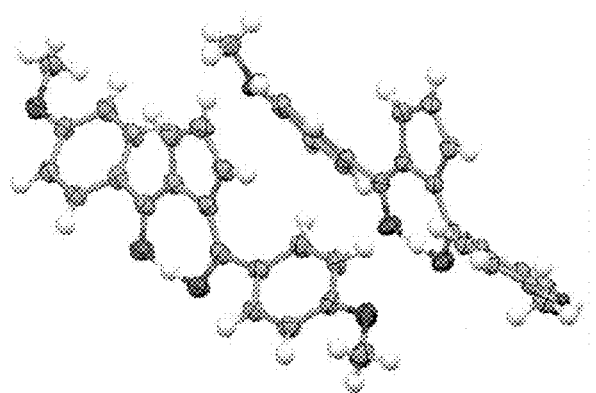
FIG. 4 represents the molecular structure of ligand 1-4-methoxybenzoyl-6-hydroxy-6-4-methoxyphenylfulvene.

Cristallography. Crystals were obtained by slow evaporation of a saturated solution of ligand in THF. The crystal structure is displayed in FIG. 4 and the ligand is characterised as follows.

| | |
|---|---|
| Empirical formula | C$_{21}$H$_{18}$O$_4$ |
| Formula weight | 334.35 |
| Temperature | 293(2) K |
| Wavelength | 0.071073 nm |
| Crystal system, space group | Monoclinic, P 21/a |
| Unit cell dimensions | a = 1.58788(3) nm   alpha = 90 deg. |
| | b = 1.18158(2) nm   beta = 104.6490(10) deg. |
| | c = 1.80453(3) nm   gamma = 90 deg. |
| Volume | 3.27561(10) nm$^3$ |
| Z, Calculated density | 8, 1.356 Mg/m$^3$ |
| Absorption coefficient | 0.093 mm$^{-1}$ |
| F(000) | 1408 |
| Crystal size | 0.55 x 0.44 x 0.4 mm |
| Theta range for data collection | 2.61 to 27.49 deg. |
| Limiting indices | −20 <= h <= 20, −15 <= k <= 15, −23 <= l <= 23 |
| Reflections collected unique | 14636/7500 [R(int) = 0.0286] |
| Completeness to theta | = 27.49   99.8% |
| Absorption correction | None |
| Refinement method | Full-matrix least-squares on F$^2$ |
| Data/restraints/parameters | 7500/0/457 |
| Goodness-of-fit on F^2 | 1.060 |
| Final R indices [I > 2sigma(I)] | R1 = 0.0485, wR2 = 0.1221 |
| R indices (all data) | R1 = 0.0710, wR2 = 0.1361 |
| Largest diff. peak and hole | 0.352 and −0.406 e.A$^{-3}$ |

Preparation of Ligand G: 1-3,4,5-trimethoxybenzoyl-6-hydroxy-6-3,4,5-trimethoxyphenylfulvene

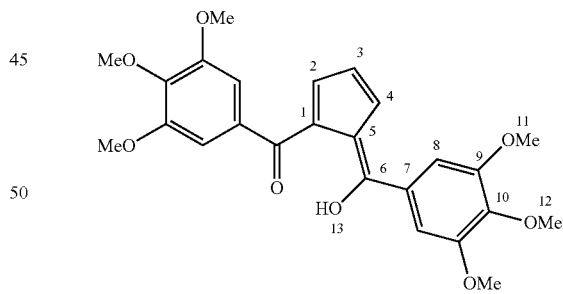

C$_{25}$H$_{26}$O$_8$
Mol. Wt.: 454,47
C, 66.07: H, 5.77; O, 28.16
Yellow solid
Yield: 28%

Cyclopentadienyl lithium was prepared from 14.5 mmol of just distilled cyclopentadiene and 14.5 mmol of butyl lithium. A solution of 2.230 g (9.7 mmol) of 3,4,5-trimethoxybenzoyl chloride in 20 mL of anhydrous ether was added dropwise to a solution of 14.5 mmol of cyclopentadienyl lithium in 20 mL of anhydrous ether, at a temperature of 0° C. The yellow mixture was placed under stirring overnight at room tempera ture (about 25° C.). The solvent was evaporated under vacuum and the remaining solid was treated with 20 mL of an acid HCl solution (5% in water) overnight. The product was extracted with 20 mL of ethyl acetate, purified on silica gel (Ether 100%) and dried on MgSO$_4$ to afford 614 mg of yellow solid with a yield of 28%.

The ligand was characterised as follows.

$^1$H NMR (CDCl$_3$, 200 MHz, ppm) δ: 18.51 (1H, s, O$^{13}$H), 7.35 (2H, d, J=0.02 Hz, C$^2$H and C$^4$H), 7.06 (4H, s, C$^8$H), 6.51 (1H, t, J=0.02, C$^3$H), 3.95 (6H, s, C$^{12}$H), 3.92 (12H, s, C$^{11}$H).

$^{13}$C NMR (CDCl$_3$. 50 MHz, ppm) δ: 185.23 (C$^6$), 162.68 (C$^7$), 153.26 (C$^9$), 144.22 (C$^2$ and C$^4$), 133.11 (C$^{10}$), 124.54 (C$^1$ and C$^5$), 12.3.28 (C$^3$), 107.85 (C$^8$), 61.44 (C$^{12}$), 56.76 (C$^{11}$).

HRMS: Calcd. for M$^+$ (C$_{21}$H$_{18}$O$_4$) m/z=334.12051. found 334.1217.

Anal. Calcd for C$_{25}$H$_{26}$O$_8$: C, 66.07; H, 5.77; O: 26.16 found C, 65.28; H, 5.82.

Preparation of Ligand H:
1-2-furoyl-6-hydroxy-6-2-furanefulvene

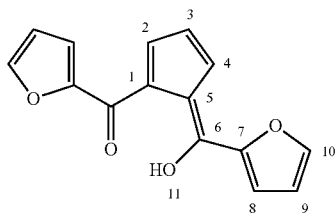

C$_{15}$H$_{10}$O$_4$
Mol. Wt.: 254,24
C, 70.86; H, 3.96; O: 25.17
Red orange solid
Yield: 21%

Cyclopentadienyl lithium was prepared from 14.5 mmol of just distilled cyclopentadiene and 14.5 mmol of butyl lithium. A solution of 1.264 g (9.7 mmol) of 2-furoyl chloride in 20 mL of anhydrous ether was added dropwise to a solution of 14.7 mmol of cyclopentadienyl lithium in 20 mL of anhydrous ether, at a temperature of 0° C. The orange mixture was placed under stirring overnight at room temperature (about 25° C.). The solvent was evaporated under vacuum and the remaining solid was treated with 20 mL of an acid HCl solution (5% in water) overnight. The product was extracted with 20 mL of ethyl acetate, purified on silica gel (Et$_2$O/heptane, 70/30 AIT flash chromatography) and dried on MgSO$_4$ to afford 260 mg of yellow solid with a yield of 21%.

The ligand was characterised as follows.

$^1$H NMR (CDCl$_3$, 200 MHz, ppm) δ: 18.49 (1H, s, O$^{11}$H), 8.14 (2H, d, J=0.02 Hz, C$^{10}$H), 7.71 (2H, s, C$^8$H), 7.39 (2H, d, J=0.02, C$^2$H and C$^4$H), 6.62 (2H, t, J=0.01, C$^9$H), 6.60 (1H, t, C$^3$H).

$^{13}$C NMR (CDCl$_3$. 50 MHz, ppm) δ: 169.60 (C$^6$), 152.31 (C$^{10}$), 147.24 (C$^2$ and C$^4$), 124.45 (C$^3$), (C$^1$ and C$^5$), 120.12 (C$^9$), 112.83 (C$^8$).

HRMS: Calcd. for M$^+$ (C$_{15}$H$_{10}$O$_4$) m/z=234.16198. found 234.1640.

Anal. Calcd for C$_{15}$H$_{10}$O$_4$: C, 70.86; H, 3.96; O: 25.17 found C, 70.50; H, 4.17.

Preparation of Ligand I: 1-2-acetoxybenzoyl-6-hydroxy-6-2-acetoxyphenylfulvene

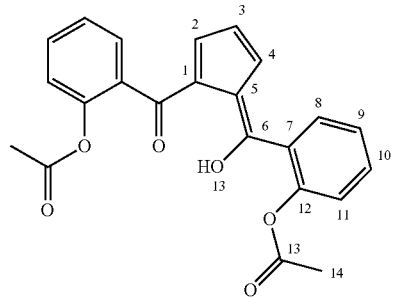

C$_{23}$H$_{18}$O$_6$
Mol. Wt.: 390,39
C, 70.76; H, 4.65; O, 24.59
Yellow solid
Yield: 18%

Cyclopentadienyl lithium was prepared from 14.5 mmol of just distilled cyclopentadiene and 14.5 mmol of butyl lithium. A solution of 1.950 g (9.81 mmol) of O-acetylsalicyloyl chloride in 20 mL of anhydrous ether was added dropwise to a solution of 14.7 mmol of cyclopentadienyl lithium in 20 mL of anhydrous ether, at a temperature of 0° C. The dark brown mixture was placed under stirring overnight at room temperature (about 25° C.). The solvent was evaporated under vacuum and the remaining solid was treated with 20 mL of an acid HCl solution (5% in water) overnight. The product was extracted with 20 mL of ethyl acetate, purified on silica gel (Ether/heptane, 2:1) and dried on MgSO$_4$ to afford 350 mg of yellow solid with a yield of 18%.

The ligand was characterised as follows.

$^1$H NMR (CDCl$_3$, 200 MHz, ppm) δδ 18.06 (1H, s, O$^{15}$H), 7.22-7.60 (8H, m, C$^8$H, C$^9$H, C$^{10}$H and C$^{11}$H), 7.09 (2H, d, J=0.02 Hz, C$^2$H and C$^4$H), 6.43 (1H, s, C$^3$H), 2.18 (6H, s, C$^{14}$H).

$^{13}$C NMR (CDCl$_3$. 50 MHz, ppm) δ: 182.76 (C$^6$), 169.63 (C$^{13}$), 148.84 (C$^7$), 142.92 (C$^2$ and C$^4$), 131.97 (C$^8$), 131.33 (C$^3$), 130.68 (C$^1$ or C$^5$), 125.86 (C$^{11}$), 125.66 (C$^{12}$), 124.16 (C$^{10}$), 124.99 (C$^9$), 30.12 (C$^{14}$)

HRMS: Calcd. for M$^+$ (C$_{23}$H$_{18}$O$_6$) m/z=390.11034. found 390.1087.

Calcd. for [M—COCH$_2$]$^+$ (C$_{21}$H$_{16}$O$_3$) m/z=348.09977. found 348.0965

Calcd. for (M—CH$_3$COOH) (C$_{21}$H$_{14}$O$_4$) m/z=330.08921. found 330.0861

Anal. Calcd for C$_{23}$H$_{18}$O$_6$: C, 70.76, H, 4.65, O: 24.59 found C, 71.17; H, 4.89.

Preparation of Metallic Complexes from Neutral Fulvenes.
Chromium Complexes.
CrCl$_3$/Ligand A Complex.

9.37 mg (40 µmol) of ligand A and 7.49 mg (20 µmol) of CrCl$_3$.3THF were introduced in a Schlenk with 200 µL of THF. The mixture was placed under stirring for 2 h at room temperature. The solvent was evaporated under vacuum overnight to yield a dark brown solid.

CrCl$_3$/Ligand H Complex.

10.17 mg (40 µmol) of ligand H and 7.49 mg (20 µmol) of CrCl$_3$.3THF were introduced in a Schlenk with 200 µL of THF. The mixture was placed under stirring for 2 h at room temperature. The solvent was evaporated under vacuum overnight to yield a red solid.

CrCl$_2$/Ligand H Complex.

10.17 mg (40 µmol) of ligand H and 2.46 mg (20 µmol) of CrCl$_2$ were introduced in a Schlenk with 200 µL of THF. The mixture was placed under stirring for 2 h at room temperature. The solvent was evaporated under vacuum overnight to yield a red solid.

Nickel Complexes.

Ni(OAc)$_2$/Ligand A Complex.

9.37 mg (40 µmol) of ligand A and 4.98 mg (20 µmol) of Ni(OAc)$_2$ were introduced in a Schlenk with 200 µL of THF. The mixture was placed under stirring for 2 h at room temperature. The solvent was evaporated under vacuum overnight to yield a yellow-green solid.

Ni(OAc)$_2$/Ligand E Complex.

18.18 mg (40 µmol) of ligand E and 4.98 mg (20 µmol) of Ni(OAc)$_2$ were introduced in a Schlenk with 200 µL of THF. The mixture was placed under stirring for 2 h at room temperature. The solvent was evaporated under vacuum overnight to yield a yellow-green solid.

Preparation of Metallic Complexes from Deprotonated Fulvenes.

CrCl$_3$/Ligand A– Complex.

Ligand A was first deprotonated with NaH.

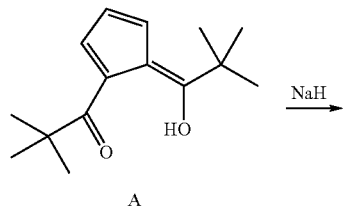

A

NaH →

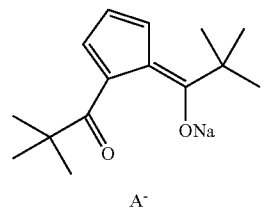

A⁻

9.37 mg (40 µmol) of ligand A and 0.96 mg (40 µmol) of NaH were introduced in a Schlenk with 400 µL of THF. The mixture was placed under stirring for a period of time of 1 h at room temperature. The solvent was evaporated under vacuum to yield a light brown solid. 7.49 mg (20 µmol) of CrCl$_3$.3THF were then introduced in the Schlenk with 200 µL of THF and the mixture was placed under stirring for a period of time of 2 h at room temperature. The solvent was evaporated under vacuum overnight to afford a dark yellow-brown solid. The complex is soluble in THF, dichloromethane and toluene.

The complex was recrystallised by slow evaporation of a saturated solution of the complex in toluene. The crystals obtained were suitable for X-Ray analysis.

Anal. Cald for C$_{34}$H$_{50}$O$_5$ClCr: C, 65.21; H, 8.05. found C, 64.83; H, 8.15.

Figure 5:
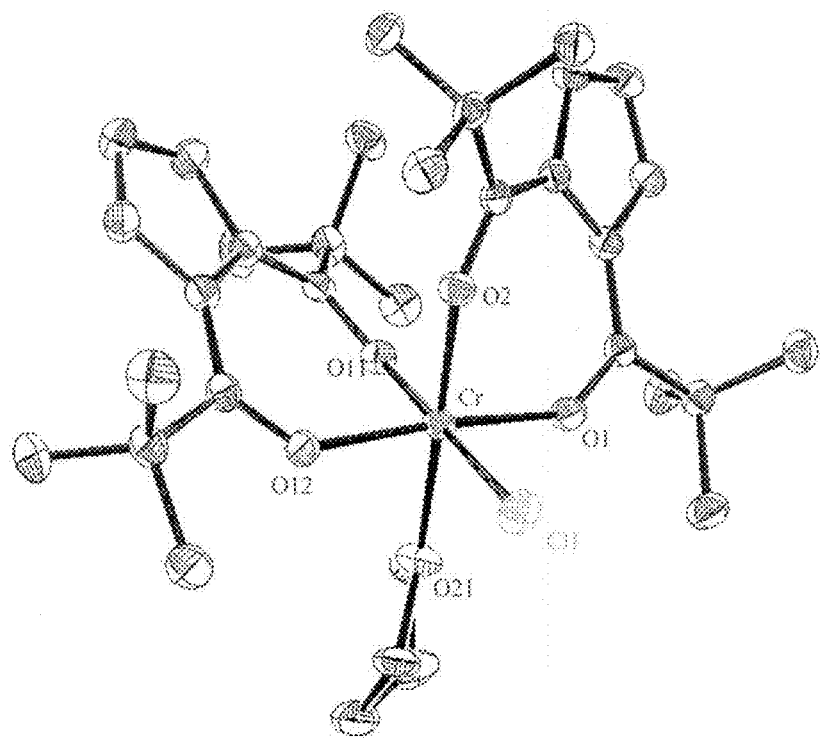
FIG. 5 represents the crystal structure of the deprotonated chromium complex prepared from deprotonated ligand 1-neopentyl-6-hydroxy-6-tertbutylfulvene and metallic salt $CrCl_3$.

The complex crystallises in a triclinic environment with space group P-1. The chromium atom is coordinated to 2 molecules of bidentate fulvene of LX type each being coordinated by its 2 oxygen atoms. The chromium atom is further coordinated by a chlorine atom and a THF molecule. This can be seen in FIG. 5. The complex is characterised as follows.

| | |
|---|---|
| Empirical formula | C$_{34}$H$_{50}$ClCrO$_5$ |
| Formula weight | 626.19 |
| Temperature | 120(2) K |
| Wavelength | 0.071073 nm |
| Crystal system, space group | Triclinic, P −1 |
| Unit cell dimensions | a = 0.95512(2) nm   alpha = 93.0100(10) deg. |
| | b = 1.09349(3) nm    beta = 91.3950(10) deg. |
| | c = 1.70208(5) nm gamma = 112.2880(10) deg. |
| Volume | 1640.71(7) A3 |
| Z, Calculated density | 2, 1.268 Mg/m3 |
| Absorption coefficient | 0.468 mm-1 |
| F(000) | 670 |
| Crystal size | 0.5 x 0.3 x 0.06 mm |
| Theta range for data collection | 2.65 to 27.57 deg. |
| Limiting indices | −12 <= h <= 12, −14 <= k <= 13, −22 <= l <= 22 |
| Reflections collected/unique | 13520/7501 [R(int) = 0.0653] |
| Completeness to theta = 27.57 | 98.8% |
| Absorption correction | None |
| Refinement method | Full-matrix least-squares on F2 |
| Data/restraints/parameters | 7501/0/371 |
| Goodness-of-fit on F^2 | 1.047 |
| Final R indices [l > 2sigma(l)] | R1 = 0.0700, wR2 = 0.1771 |
| R indices (all data) | R1 = 0.0870, wR2 = 0.1887 |
| Extinction coefficient | 0.039(4) |
| Largest diff. peak and hole | 1.048 and −0.631 e.A−3 |

CrCl$_3$/Ligand H− Complex.

Ligand H was first deprotonated with NaH.

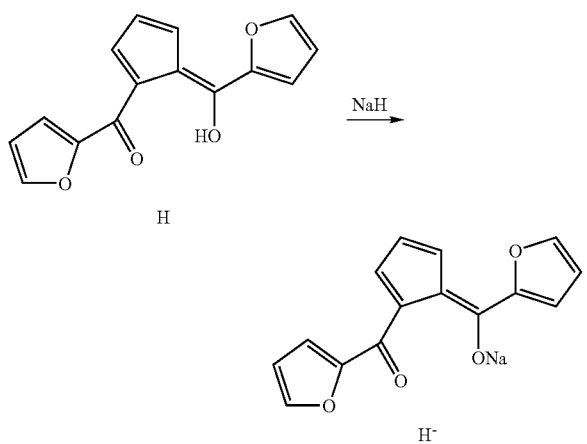

10.17 mg (40 μmol) of ligand H and 0:96 mg (40 μmol) of NaH were introduced in a Schlenk with 400 μL of THF. The mixture was placed under stirring for a period of time of 1 h at room temperature. The solvent was evaporated under vacuum to yield a yellow solid. 7.49 mg (20 μmol) of CrCl$_3$.3THF were then introduced in the Schlenk with 200 μL of THF and the mixture was placed under stirring for a period of time of 2 h at room temperature. The solvent was evaporated under vacuum overnight to afford a dark red solid.

CrCl$_2$/Ligand H− Complex.

10.17 mg (40 μmol) of ligand H and 0.96 mg (40 μmol) of NaH were introduced in a Schlenk with 400 μL of THF. The mixture was placed under stirring for a period of time of 1 h at room temperature. The solvent was evaporated under vacuum to yield a yellow solid: 2.46 mg (20 μmol) of CrCl$_2$ were then introduced in the Schlenk with 200 μL of THF and the mixture was placed under stirring for a period of time of 2 h at room temperature. The solvent was evaporated under vacuum overnight to afford a dark red solid.

Homogeneous Polymerisation of Ethylene.

The metallic catalyst component were activated with 3.25 mL of methylaluminoxane (MAO)(30% in toluene). The solution was stirred for 5 minutes and then diluted with 1.75 mL of toluene. The reactor was dried under nitrogen at a temperature of 110° C. for a period of time of 30 minutes. The reactor was brought to a polymerisation temperature of 35° C. and 50 mL of toluene were added to the reactor under nitrogen. A scavenger solution consisting of 1 mL of MAO (30% in toluene) and 4 mL of toluene was added to the reactor and the solution was stirred for a few minutes. The solution of activated catalyst was added to the reactor under nitrogen. The flux of nitrogen was interrupted, the reactor was purged and placed under an ethylene pressure of 15 bars. It was placed under stirring for a period of time of 1 h. The reactor was purged and the polymerisation was stopped by adding a 10% solution of MeOH/HCl. The polymer was washed 3 times with 30 mL of MeOH and 3 times with 30 mL of acetone. The polymer was dried under vacuum overnight at room temperature. The results are summarised in Table I for the chromium-based catalyst systems, and in table II for the nickel-based catalyst systems.

TABLE I

| Catalyst | Mass PE (g) | Activity (kg$_{PE}$/(mol · h)) | Tm (° C.) | Mp | Mn | Mw | Ip |
|---|---|---|---|---|---|---|---|
| CrCl$_3$/A | 1.20 | 60 | 125 | 689 | 1 453 | 129 217 | 89 |
| CrCl$_3$/H | 4.75 | 237 | 130 | 474 | 1 874 | 214 323 | 114 |
| CrCl$_2$/H | 5.56 | 278 | 133 | 538 | 1 452 | 240 331 | 165 |
| CrCl$_3$/H− | 5.91 | 295 | 128 | 758 | 1 967 | 333 164 | 169 |
| CrCl$_2$/H− | 6.47 | 324 | 131 | 804 | 2 061 | 388 029 | 188 |
| CrCl$_3$/A− | 8.38 | 419 | 129 | i | i | i | i | i: insoluble polymer

For all polymerisations, the conditions were as follows:

Cr 20 μmol, ligand 40 μmol, polymerisation temperature 35° C., ethylene pressure 15 bars, 1000 eq. MAO.

solvent: toluene, polymerisation time 1 h.

TABLE II

| | m$_{PE}$ (g) | Activity kg$_{PE}$/(mol · h) | Consom. (kg$_{C2H4}$/(mol · h)) | Distributions oligo. (%) | | |
|---|---|---|---|---|---|---|
| | | | | C4 (α) | C6 | C8 |
| Ni(OAc)$_2$ | 0.021 | 1.05 | 580 | 73.2 (49) | 21.9 | 4.9 |
| Ni(OAc)$_2$/A | 0.027 | 1.35 | 641 | 71.4 (50) | 25.4 | 3.2 |
| Ni(OAc)$_2$/E | 0.028 | 1.4 | 890 | 57.2 (45) | 36.4 | 6.5 |

For all polymerisations, the conditions were as follows:

Cr 20 μmol, ligand 40 μmol, polymerisation temperature 30° C., ethylene pressure 15 bars, 1000 eq. MAO, solvent: toluene, polymerisation time 1 h.

The highest activity was obtained with the catalyst system based on CrCl$_3$/ligand A−. Its activity has been studied as a function of temperature and of ethylene pressure. The results are displayed in Table III.

TABLE III

| Activity (kg$_{PE}$/(mol · h)) | | Pressure (bars) | | |
|---|---|---|---|---|
| | | 15 | 24 | 45 |
| Temp. (° C.) | 35 | 486 | 512 | 588 |
| | 55 | 292 | 538 | 602 |
| | 85 | 47 | 119 | 254 |

The conditions were as follows:
Cr 10 µmol,
ligand 20 µmol,
1000 eq. MAO,
solvent: toluene,
polymerisation time 1 h.

It can be concluded that the activity of the catalyst system increases with increasing pressure and decreases when the temperature is increased.

The same catalyst system based on $CrCl_3$/ligand A– was used for additional ethylene polymerisations under the following conditions:

Complexation time: 12 h,
1000 eq. MAO,
solvent: toluene,
polymerisation time 1 h,

TABLE IV

| Catalyst amount (µmol) | Temperature (° C.) | Pressure (bars) | m PE (g) | Activity ($kg_{pE}$/ (mol · h) | Consom. ($kg_{C2H2}$/ (mol · h) |
|---|---|---|---|---|---|
| 5 | 35 | 45 | 15.18 | 3 077 | n.m. |
| 5 | 25 | 45 | 20.34 | 4 069 | n.m. |
| 2.5 | 35 | 45 | 9.10 | 3 642 | n.m. |
| 2.5 | 35 | 45 | 7.78 | 3 112 | 3 000 |
| 2.5 | 25 | 45 | 8.90 | 3 560 | n.m. |
| 2.5 | 25 | 45 | 10.10 | 4 040 | 4 430 |
| 1.0 | 25 | 45 | 5.298 | 5 298 | n.m. |
| 3.26 | 0 | 45 | 5.36 | 1 645 | n.m. |
| 3.26 | 0 | 45 | 5.34 | 1 639 | 4 982 | n.m. = not measured

Polymerisation of Ethylene with Supported Catalyst Systems.

The activity of the unsupported $CrCl_3$/ligand A– catalyst system was evaluated in heptane. There was not a selective amount of ethylene present in the polyethylene. The polymerisation conditions were as follows:
complexation time: 12 hours,
5 µmol of ligand with 2.5 µmol of Cr,
polymerisation temperature: 25° C.,
polymerisation pressure: 45 bars,
1000 equ. of MAO,
solvent: heptane,
polymerisation time: 1 hour.
The results are displayed in Table V.

TABLE V

| mPE (g) | Activity ($kg_{PE}$/(mol · h) | Consom. ($kg_{C2H4}$/(mol · h)) | Tm (° C.) |
|---|---|---|---|
| 3.40 | 1 360 | 3 214 | 139 |

Impregnation of the Catalyst on Silica/MAO.

5 µmol of complex $CrCl_3$/A⁻ were dissolved in 600 µl of toluene and then introduced in a schlenk with 100 mg of silica/MAO (50 $µmol_{Cr}/g_{Si}$) under stirring for a period of time of 30 minutes. The impregnated silica was filtered and washed either with once 600 µl of toluene and three times with 600 µl of heptane (condition 1) or three times with 600 µl of heptane (condition 2).

Polymerisation of Ethylene with Impregnated silica/MAO.

The reactor was dried under nitrogen for a period of time of 30 minutes and at a temperature of 90° C. 50 mL of heptane were then introduced into the reactor with 100 mL of scavenger, MAO (30%) diluted in 5 mL of heptane, at a temperature of 25° C. 50 mg of silica, containing about 2.5 µmol of activated catalyst (50 $µmol_{Cr}/g_{SiO2}$) were introduced into the reactor with 5 mL of heptane. The polymerisation reaction was carried out at a temperature of 25° C. under an ethylene pressure of 45 bars and for a period of time of 1 hour for conditions 1 and 2. The results are displayed in Table VI.

TABLE VI

| | m PE (g) | Activité ($kg_{PE}$/(mol · h) | Consom. ($kg_{C2H4}$/(mol · h) | Activité ($g_{PE}$/($g_{si}$ · h)) | Consom. ($g_{C2H4}$/($g_{si}$ · h)) | Tm (° C.) |
|---|---|---|---|---|---|---|
| Cond. 1 | 1.02 | 408 | 3 993 | 20.4 | 200 | 139 |
| Cond. 2 | 3.42 | 1 368 | 3 530 | 68.4 | 177 | 133 |

The complexation time was of 12 hours.
Polymerisation of Alpha-Olefins.

The unsupported catalyst system $CrCl_3$/A⁻ was used for the polymerisaton of hexene with the following conditions: $CrCl_3$/A⁻/MAO/hexene=1/100/2000. After a period of time of 24 hours and a polymerisation temperature of 30° C. the yield was of about 2%.

The invention claimed is:

1. A method for preparing a metallic complex comprising:
providing a metallic precursor $MZ_n$ wherein M is a metal Group 7 to 11 of the Periodic Table, Z is a negatively charged counter-anion and n is the valence of M;
complexing the metallic precursor with a ligand of formula:

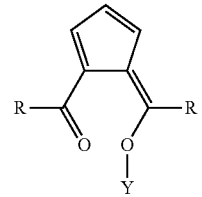

wherein both R are the same and are selected from aryl, alkyl arylalkyl, alkylaryl having at most 20 carbon atoms, and Y is an element Group 1 of the Periodic Table; and
retrieving a metallic complex.

2. The method of claim 1, wherein R is alkyl, substituted or unsubstituted phenyl group, CPh2 wherein phenyl group Ph is substituted or unsubstituted or furan-containing group.

3. The method of claim 2, wherein R is tert-butyl or furan.

4. The method of claim 1, wherein Y is H or Na.

5. The method of claim 1, wherein M is Ni.

6. The method of claim 1, wherein Z is halogen or acetate.

7. The method of claim 1, wherein the ligand is deprotonated with a base prior to complexation.

8. The method of claim 7, wherein the base is NaH.

9. A metallic complex obtained by the method of claim 1.

10. An active catalyst comprising the metallic complex of claim 9, an activating agent having an ionising action and optionally a support.

11. The active catalyst system of claim 10, wherein the activating agent is methylaluminoxane.

12. A method for oligomerising or for homo- or co-polymerising ethylene and alpha-olefins comprising:

injecting the active catalyst of claim 10 into a reactor;
injecting the monomer and optional comonomer into the reactor;
maintaining the reactor under polymerisation conditions to form a polymerization product selected from oligomers, polymer or combinations thereof; and
retrieving the product from the reactor.

13. The method of claim 12, wherein the monomer and comonomer are selected from ethylene or propylene.

14. A method for preparing an active catalyst system comprising:
providing a hydroxyl-carbonyl fulvene ligand;
optionally deprotonating the ligand with a base;
complexing the ligand with a metallic salt $MZ_n$ in a solvent, wherein M is a metal of Group 7 to 11 of the Periodic Table, wherein Z is a negatively charged counter-anion, and wherein n is the valence of M;
retrieving a catalyst component;
optionally depositing the catalyst component on a support;
activating the catalyst component with an activating agent having an ionising action;
optionally adding a scavenger; and
retrieving an active oligomerisation or polymerisation catalyst system.

\* \* \* \* \*